(12) United States Patent
Shukla et al.

(10) Patent No.: US 7,442,854 B2
(45) Date of Patent: Oct. 28, 2008

(54) HIGH YIELDING MULTIPLE DISEASE RESISTANT/TOLERANT STABLE VARIETY 'MADAKINI' OF OPIUM POPPY

(75) Inventors: Sudhir Shukla, Lucknow (IN); Sant Prasad Singh, Lucknow (IN); Harikesh Bahadur Singh, Lucknow (IN); Palpu Pushpangadan, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 306 days.

(21) Appl. No.: 11/009,697

(22) Filed: Dec. 13, 2004

(65) Prior Publication Data

US 2006/0130186 A1    Jun. 15, 2006

(51) Int. Cl.
*A01H 5/00* (2006.01)
*A01H 5/10* (2006.01)
(52) U.S. Cl. .................................................. 800/298
(58) Field of Classification Search ................ 800/298, 800/295
See application file for complete search history.

(56) References Cited

U.S. PATENT DOCUMENTS 6,534,696 B1    3/2003    Dhawan et al.
6,723,894 B2    4/2004    Fist et al.

OTHER PUBLICATIONS

Alam et al., "Damping-off, a new disease of opium poppy caused by *Pythium dissotocum*," Indian Phytopathology, 1996, vol. 49, No. 1, pp. 94-97.
Anonymous, Indian Pharmacopoeia, Government of India, Ministry of Health & Family Welfare, vol. II, 1996.
Bajpai et al., "Identification of Indian Landraces of Opium Poppy *Papaver somniferum* Resistant to Damping-off and Downy Mildew Fungal Diseases," J. Phytopathology, 1999, vol. 147, pp. 535-538.
Chadha et al., Ed., Advances in Horticulture, Medicinal and Aromatic Plants, vol. 11, 1995, Table of Contents.
Eckey et al., Vegetable Fats and Oils, 1954, pp. 447-449.
Food and Chemical Toxicology, vol. 30, Jan. 1992, Table of Contents.
Hartman et al., "Evaluation of Perennial *Glycine* Species for Resistance to Soybean Fungal Pathogens That Cause Sclerotinia Stem Rot and Sudden Death Syndrome," Crop Sci., 2000, vol. 40, pp. 545-549.
Kothari et al., "Downy mildew of opium poppy in rajasthan," Indian Phytopathology, Dec. 1970, vol. 23, pp. 676-688.
Kothari et al., Powdery milder of opium poppy in rajasthan and its control, Indian Phytopathology, Mar. 1972, vol. 25, pp. 36-39.
Kumar et al., "Classical to molecular concepts of flax—flax rust interaction," Indian J. Plant Pathol., 2003, vol. 21, Nos. 1 and 2, pp. 1-11.
Nergiz et al., "The Proximate Composition and some Minor Constituents of Poppy Seeds," J. Sci. Food. Agric., 1994, vol. 66, pp. 117-120.
Sattar et al., "Screening of opium poppy (*Papaver simniferum*) germplasm for disease resistance," Current Research on Medicinal and Aromatic Plants, 1995, vol. 17, pp. 315-320.
Shukla et al., "Opium poppy 'BROP1'," Indian Hort., 1994, vol. 39, No. 4, pp. 7-9.
Singh et al., "Fatty acid composition of opium poppy (*Papaver somniferum*) seed oil," Indian Journal of Agricultural Sciences, May 1990, vol. 60, No. 5, pp. 358-359.

*Primary Examiner*—David H Kruse
*Assistant Examiner*—Keith O. Robinson
(74) *Attorney, Agent, or Firm*—Foley & Lardner LLP

(57) ABSTRACT

The invention relates to the development of a novel high yielding multiple disease resistant/tolerant stable variety of opium poppy (*Papaver somniferum* L. 2n=22) christened 'Madakini'.

2 Claims, 4 Drawing Sheets

BR007 (Parent 1)

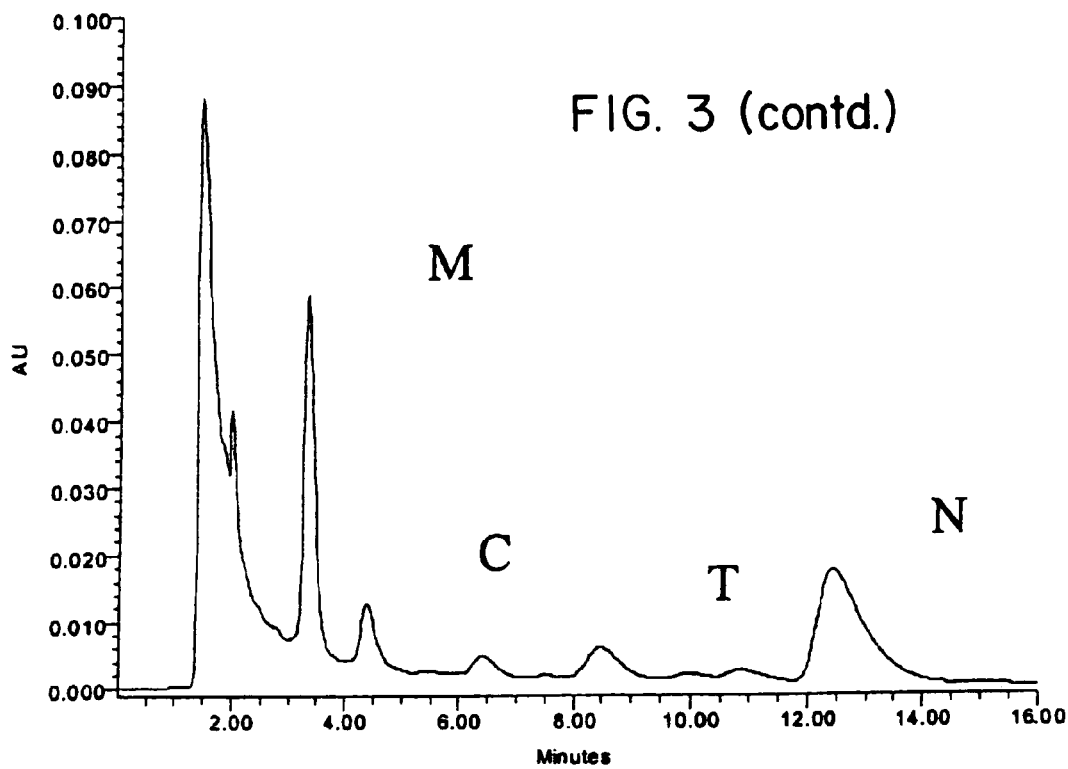
FIG. 3 (contd.)
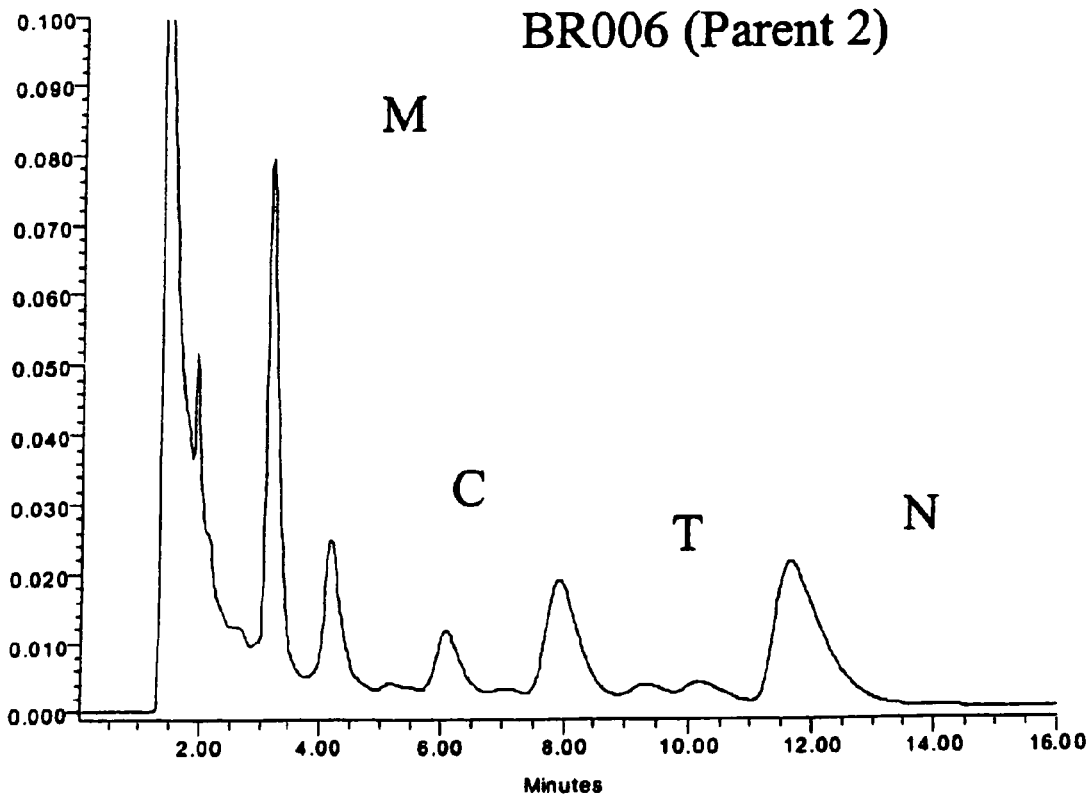
BR006 (Parent 2)
Madakini

HIGH YIELDING MULTIPLE DISEASE RESISTANT/TOLERANT STABLE VARIETY 'MADAKINI' OF OPIUM POPPY

FIELD OF THE PRESENT INVENTION

The present invention relates to the development of multiple disease resistant and high opium yielding variety of opium poppy (*Papaver somniferum* L.) 'Madakini'. More specifically the innovation relates to the development of high opium, seed and morphine content variety of opium poppy through hybridization of two high yielding cultivars followed by repeated selection up to F6 generation and evaluation and further evaluation for four characters up to nine years in preliminary, initial and multilocational trials under natural conditions. The variety 'Madakini' was further tested for multiple disease resistant in natural epiphytotic conditions. The variety is resistant to downy mildew caused by *Peronospora arborescens* and also resistant to powdery mildew caused by *Erysiphe polygoni* and tolerant to collar rot, damping off, stem/capsule rot and leaf spot and blight which are caused by *Sclerotium rolfsii, Pythium dissotocum, Sclerotinia sclerotioum* and *Alternaria alternata* respectively. The variety is distinct, stable and uniform and is fully suitable for commercial cultivation to recover high opium yield.

BACKGROUND OF THE PRESENT INVENTION

Opium Poppy (*P. somniferum* L.) is one of the oldest and most important medicinal plant, known to mankind since centuries. Its commercial cultivation lies in several European and Asian countries under the strict control of International Narcotics Control Bureau (INCB), Vienna. The opium is obtained in the form of latex by the incision of unripe capsule, is a chief source of number of alkaloids of great medicinal and economic uses in pharmaceutical industries. Out of these alkaloids, morphine, codeine, thebaine, narcotine and papaverine are the major ones, used mainly for the preparation of pain killing drugs. India is one of the world's largest producers of licit opium (Singh et al., Advances in Horticulture-Medicinal and Aromatic Plants, Vol.11, ICAR Publication, N. Delhi, 436-474,1995). Beside, meeting the domestic demands, opium alkaloids and their derivatives are being exported up to Rs.1320 million in the recent years. The area under crop cultivation in India varies according the world demand put up through United Nations.

During 2000, 35,271 ha land was under opium poppy cultivation and 1302 MT opium (90% consistency) was produced. The use of opium alkaloids has increased steadily much in recent years and global demand for codeine and thebaine increased manifold due to its non-narcotic properties. Thebaine utilization in pharmacopoeia has increased about 10 folds from 1994 (5.8 MTs) to 2000 (45.6 MTs). Similarly consumption of codeine for drug purposes has increased from 160 MT in 1981-82 to 169 in 2000, while its derivatives mainly dihydrocodeine and hydrocodeine has increased five times to a recent level of 80 MTs in 2000. However, the morphine apart from being used in medical treatment is predominantly converted into codeine which consumption has increased from 200 MTs in 1990 to 256 MTs in 2000 (Anonymous, Govt. of India, Ministry of Finance, Deptt. of Revenue, 2002, Shukla and Singh, Herbal Drugs and Biotechnology (Ed. P. C. Trivedi), Pointer Publishers, Jaipur, India, pp. 210-239, 2004).

The opium poppy is being primarily grown for opium latex and its derivatives but its seeds are also equally important by product due to rich in protein (up to 24%) and mineral content and are widely used in various preparation in confectionery industries, while in European countries it is grown for edible seed and seed oil (Eckey, Reinhold Publishing Co., Hy:447-449, 1954; Puspangadan and Singh, Wood Head Publishing, U.K. 261-268, 2001). Seeds are only part which are devoid of any alkaloids and is considered as aphrodisiac, constipating (Nerglz and Otles, J. Sci. Food Agric. 66: 117, 1994) and anti carcinogenic (Aruna, Food Chem. Toxicol. 30:11,1992). The seeds are rich source of edible oil (42.50%) with unsaturated fatty acids viz. palmitic acid (8.9-21.48%), stearic acid (1.4-10.8%), oleic acid (13.22-36.70%), linoleic acid (41.0-68%) and linolenic acid (0.00-9.40%) (Singh et al., Indian J. Agric. Sci. 60: 358-359,1990). Linoleic acid checks the blood cholesterol in human system and prevents atherosclerosis and heart attack (Singh et al., Advances in Horticulture-Medicinal and Aromatic Plants, vol.11, ICAR Publication, N. Delhi, 436-474,1995). Despite these uses, other parts of poppy plants are also used in several preparations (Singh et al., Advances in Horticulture-Medicinal and Aromatic Plants, vol. 11, ICAR Publication, N. Delhi, 436-474,1995).

Opium poppy crop is affected by several fungal pathogens causing losses in yield and a quantitative decrease in alkaloids content. Out of them, one of the major diseases, downy mildew caused by *Pernospora arborescense* is the most destructive and is fairly widespread affecting most of the common varieties of opium poppy cultivated in north India (Kothari and Prasad, Indian Phytopath. 23: 676-688, 1970; Sattar et al., CROMAP 17:315-320,1995; Bajpai et al., J. Phytopath. 147: 535-538,1999). Powdery mildew caused by *Erysiphae polygoni* recorded from many localities and causes serious damage in Rajasthan, India (Kothari and Prasad, Indian Phytopath. 25: 36-39,1972). Its incidence is generally noticed at later stage of growth period and characterized by white powder on leaves and capsules. The disease damping off caused by *Pythium dissotocum* spreads rapidly in severely infected fields and kills the young plant population within 15-20 days of its appearance. Its occurrence mostly happens in misty weather conditions when humidity remains high for 8-10 days (Alam et al., Indian Phytopath. 49: 94-97,1995). The collar rot disease caused by *Sclerotium rolfsii* initially appears at the color region as well as stem of infected plants as dark brown necrotic lesions which later on resulted black in colour and toppling of the infected plants (Singh et al., Indian J. Pl. Path. 19, 1-11, 2003). Another disease stem/capsule rotting due to *Sclerotinia sclerotiorum* often attack the plants at capsule formation stage. The symptom start appearing as browning of the stem and leaf covered with lesions, which later on causes leaves fall off, capsules and stem show severe rotting (Hartman et al. Crop Sci. 40:545-549, 2000). Leaf spot and blight disease caused by *Alternaira alternata* spreads on the leaves as gray circular spots with concentric rings, which later turn black, and defoliation occurs.

Opium poppy is a most important medicinal plant but till now no any multiple disease resistant/tolerant and high opium yielding variety is available. However, in opium poppy efforts have been made towards the development of method for producing a disease resistant and high seed and husk yielding variety (Dhawan et al. 2003, U.S. Pat. No. 6,534,696). Similarly, increase in production of thebaine and oripavine from an improved poppy straw of a stably reproducing *P. somniferum* plant has been obtained (Fist et al. 2004, U.S. Pat. No. 6,723,894). Uptill now, the existing released varieties have maximum opium yield up to 54 kg/ha (Shukla et al., Indian Hort. 39(4): 7-9, 1994, Singh et al., Advances in Horticulture-Medicinal and Aromatic Plants, vol. 11, ICAR Publication, N. Delhi, 436-474,1995). Keeping it in mind, planned experiments were conducted at National Botanical Research Institute, Lucknow, India for the development of multiple disease resistant/tolerant high opium yielding variety. From the available germplasm/land races in the Institute, promising high yielding lines were screened and hybridized in a set-breeding pattern followed by repeated selection for desirable character in the advanced generations. The selected high yielding hybrids evaluated in preliminary, initial and multilocational trials along with checks under natural conditions followed by two years disease evaluation trials conducted in field with known history of sick soil for the past 20 years under natural epiphytotic conditions.

OBJECTS OF THE PRESENT INVENTION

The primary objective of the invention is to develop high opium yielding variety in opium poppy.

Another objective is to develop high seed yielding opium variety.

Yet another objective is to develop opium variety with multiple disease resistant/tolerant against common diseases in opium poppy.

A still another objective is to develop opium variety having high morphine content in opium.

SUMMARY OF THE PRESENT INVENTION

To meet the objective, the present invention provides a novel variety of opium poppy "Madakini" capable of producing high opium and seed yield. The said variety is resistant/tolerant to multiple diseases common in opium poppy. The opium latex of the variety is also rich in morphine content in comparison to the commercially existing varieties/cultivars.

DETAILED DESCRIPTION OF THE PRESENT INVENTION

Accordingly the present invention provides new and distinct, a novel high yielding multiple disease resistant/tolerant stable variety 'Madakini' of opium poppy. The variety is capable of producing high opium and seed yield with high morphine content. The seeds of the 'Madakini' variety as described herein, have been deposited with the International Deposit Authority, the National Collection of Industrial, Food and Marine Bacteria (NCIMB Ltd.), Scotland United Kingdom, under Accession No. NCIMB 41506 and may be obtained on request from the Director of the National Collection of Industrial, Food and Marine Bacteria (NCIMB Ltd.), Scotland, United Kingdom. The said variety of opium poppy is having the following morphological/agronomic characteristics.

| | |
|---|---|
| Plant height (cm) | 105-125 |
| Peduncle length (cm) | 24-28 |
| Peduncle colour (Based on Royal Horticultural Society, London (U.K.) | Green later on blackish 147C |
| Seed yield (q/ha) | 11.61-12.83 |
| Straw yield (q/ha) | 8.91-9.25 |
| Days to 50% flowering | 108-110 |
| Days to maturity | 140-142 |
| Number of capsules/plant | 3-5 |
| No. of stigmatic rays/capsule | 12-14 |
| Latex colour | Dark pink |
| No. of seeds/g | 3515-3621 |
| Seed colour | whitish |
| Seed shape | reniform |
| Leaf area (cm$^2$) | 179.2-181.8 |
| Pollen fertility | 95-98% |

| -continued | |
|---|---|
| Seed germination (%) | 94% |
| Oil content in seed (%) | 48-49% |
| Fatty acids composition: | |
| Palmitic acid | 9.0% |
| Steraic acid | 2.1% |
| Oleic acid | 18.4% |
| Linoleic acid | 70.1% |
| Linolenic acid | 0.4% |
| Unsaturated total fatty acid | 88.9% |
| Saturated fatty acids | 11.1% |
| Capsule shape | Spherical real sphere |
| Capsule surface | Smooth |
| Leaf colour (Based on Royal Horticulture Society, London, U.K.) | Green, 147B |
| Stem diameter | 1.03-1.10 cm |
| Capsule size | 14.30-14.68 cm$^2$ |
| Branches/plant | 3-6 |
| Opium yield (kg/ha) | 64-68 |
| Capsule colour (Based on Royal Horticulture Society, London, U.K.) | Green, 147B |

The invention further provides multiple disease resistance/tolerance in high yielding variety "Madakini" which exhibits reactions to various diseases as under:

| Disease | Causal organism | Ratings | Category | Scale used |
|---|---|---|---|---|
| 1. Downy mildew | Peronospora arborescense | 1-2 | resistant | 0-9 |
| 2. Damping off | Pythium dissotocum | 1-2 | tolerant | 0-4 |
| 3. Collar rot | Sclerotium rolfsii | 1-2 | tolerant | 0-4 |
| 4. Powdery mildew | Erysiphe polygoni | 1-2 | resistant | 0-4 |
| 5. Leaf spot and blight | Alternaria alternata | 1-3 | tolerant | 0-9 |
| 6. Stem/capsule rot | Sclerotinia sclerotiorum | 1-2 | tolerant | 1-5 |

The invention further provides multiple disease resistant/tolerant and high yielding variety "Madakini" of opium poppy with the following chemical features in opium latex.

| | |
|---|---|
| Morphine | 15.10-17.60% |
| Codeine | 2.53-3.15% |
| Thebaine | 1.78-2.80% |
| Narcotine | 8.67-9.47% |
| Papaverine | 0.00-0.13% |

In an embodiment of the invention the parental material for the said variety "Madakini" comprised of BR007 as the female parent and BR006 as male parent. Both parents were inbreds and selected on the basis of high opium yield and good plant type but BR007 was susceptible to the downy mildew and BR006 was highly resistant to the downy mildew. In another embodiment of the invention 0-4 scale disease rating was used for scoring collar rot disease reactions under epiphytotic conditions in field wherein 0-1 was considered resistant (0=no visible reaction; 1=infection restricted up to 1 cm length on the color region), 1.1-2.0 as tolerant (1.1=infection more than 1 cm length on the color region, 2.0=infection starts spreading in the root and shoot), 2.1-3.0 as susceptible (2.1=infection spreads downwards (root) and upwards (stem) and yellowing of lower leaves, 3.0=pronounced rotting symptoms start appearing at the color region as well as the stem of infected plants), 3.1-4.0 as highly susceptible (3.1 dark brown rotting become more prominent, 4. color region and stem become pulpy resulting into toppling of infected plants.

In another embodiment of the invention 0-4 scale was used for damping off disease reactions under epiphytotic conditions in field wherein 0-1 was considered as resistant (0=no visible reaction, 1=very few minute necrotic lesions of limited growth on roots, no chlorosis), 1.1-2.0 as tolerant (few necrotic lesions on the roots with chlorotic symptoms only on the lower leaves), 2.1-3.0 as susceptible (many dark brown necrotic lesions on the roots with distinctly visible chlorotic symptoms), 3.1-4.0 as highly susceptible (entire root system with dark brown necrotic and rotting symptoms leading to sudden death of infected seedlings).

In another embodiment of the invention 0-9 scale rating was used for scoring downy mildew reactions under epiphytotic as well as natural field conditions wherein 0-3 was considered resistant (0=no visible disease reactions; 3=less than 20% of the lower leaves covered with disease reactions), 3.1 to 5.0 as tolerant (3.1=more than 20% disease reactions on lower leaves; 5.0=less than 50% disease reactions on lower leaves), 5.1-7.0 as susceptible (5.1=more than 50% disease reactions on all the leaves; 7.0=less than 75% disease reactions on lower leaves), 7.1-9.0 as highly susceptible (7.0=more than 75% disease reactions; 9.0=premature death of the infected plant).

In another embodiment of the invention 0-4 scale rating was used for scoring powdery mildew reaction under epiphytotic as well as natural field conditions where 0-2 was considered resistant (0=no symptoms, 2=up to 30% leaf area infected), 2.1-3.0 as susceptible (2.1 =more than 60% leaf area affected, 3=up to 90% leaf area affected), 3.1-5.0 as highly susceptible (3.1=more than 90% leaf area affected, 5.0 leaves and all parts of the plant covered with powdery mildew).

In another embodiment of the invention 0-9 scale rating was used for scoring leaf spot and blight reactions under epiphytotic as well as natural field conditions wherein 0-3 was considered resistant (0=no symptoms on leaves, 3.0 gray circular spots containing concentric rings and up to 10% of the leaf area), 3.1-5.0 as tolerant (3.1=gray circular spots covering more than 10% of the leaf area, 5.0=necrotic lesions enlarge, gray circular spots covering more than 10% of the leaf area, 5.0=necrotic lesions enlarge, gray circular spots with concentric rings and a black border to cover up to 25% of the leaf area), 5.1-7.0 as susceptible (4.1=more than 25% of leaf area covered with large necrotic lesions with black border, 7.0=enlarged lesions coalesce with each other to cover up to 50% area), 7.1-9 as highly susceptible (7.1=more than 50% leaf area covered with necrotic lesions, 9.0=necrotic lesions cover more than 70% leaf area and defoliation occurs).

In another embodiment of the invention 1-5 scale rating was used for scoring stem/capsule rot reactions under epiphytotic as well as natural field conditions wherein 1-2 was considered resistant (1=no symptoms, 2=light symptoms development with slight browning of the stem and 1-20% leaf area covered with lesions), 2.1-4.0 as susceptible (1=moderate symptoms with 21-50% leaf area covered with necrotic lesions, 4=heavy symptoms with development of necrotic lesions in 51-80% leaf area, stem rotting also starts), 4.1-5 as highly susceptible (4.1=capsules show development of necrotic lesions in 50% area, 5.0=81-100% leaf area covered with lesions, leaves fall off, capsules and stem show severe rotting).

Further the method of invention of multiple disease resistant/tolerant high yielding variety "Madakini" comprises the steps:

1. Selection of high yielding pure and homozygous promising lines from the germplasm stock.
2. Hybridization of the selected parental lines in all possible combinations.
3. Raising of FI hybrids of all the combinations and selfing them to obtain F2 seeds.
4. Further raising of F2 generation of all the combinations of the crosses and selfed only the promising high yielding resistant plants of the some lines.
5. Selection of highly resistant plants with high opium, seed and morphine content in F3 and subsequent generations up to F6 generations.
6. Preliminary evaluation of 7 F7 promising uniform plant progenies along with a check in a randomized block design for 3 consecutive years.
7. Initial evaluation of two out yielding (BR007×BR006 and BR007×BR008) lines selected out of the above 7 promising lines for 3 years along with some other lines and two checks.
8. Multilocational evaluation of high yielding selected lines ((BR007×BR006 and BR007×BR008) along with other promising lines against national and local checks for three years.
9. Screening of fungal diseases in the variety "Madakini" along with both of its parents and national and local checks for two years.
10. In an embodiment, the parental material considered for hybridization program were promising high yielding genotypes.

BRIEF DESCRIPTION OF THE
ACCOMPANYING DRAWINGS

Figure 1:
FIG. 1 represents a field view of variety "Madakini".
Figure 2:
FIG. 2(a,b) represents a single plant of the variety.
Figure 2:
Figure 3:
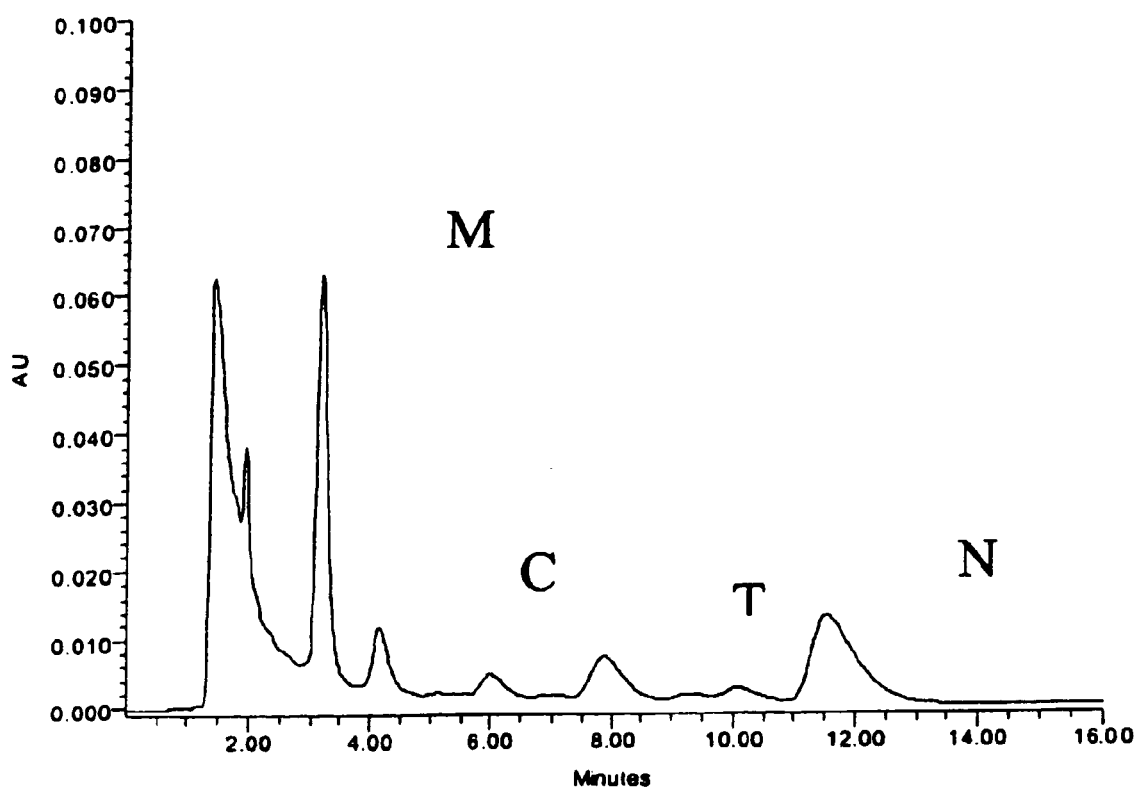

FIG. 3. Alkaloid spectrum in latex of the plant of the invented variety "Madakini" and both of its parents (BR006 and BR007).

The hybridization program for the development of high opium yielding variety was started in the year 1983. Ten distinct promising pure lines (BR001, BR002, BR003, BR004, BR005, BR006, BR007, BR008, BR009 and BR010) identified on the basis of yield performance were involved in the breeding programme.

The selected lines were hybridized among themselves in all possible combinations including reciprocals. The F1 generation was raised for each individual cross and plants were selfed to obtain F2 seeds. In the following year F2 generation was grown which showed large segregation for opium yield, seed yield and alkaloid content. Out of this F2 population, vigorous plants from the promising crosses were selfed to obtain F3 seeds. The seeds of selected plants belonging to particular cross were bulked. In F3 generation, total 22 cross progenies were grown and further selection of vigorous plants were done from the promising cross progenies, which was continued up to F6 generation. Lastly 7 promising cross progenies were short-listed which were evaluated in preliminary yield trial.

TABLE 1

Description of the variety "Madakini" in comparison to its parents.

| Sl. No | Characters | Madakini | BR006 | BR007 |
|---|---|---|---|---|
| 1 | Plant height (cm) | 105-125 | 110-118 | 94.2-108.6 |
| 2 | Peduncle length (cm) | 24-28 | 19-23 | 23-26 |
| 3 | Peduncle colour (Based on Royal Horticultural Society, London, U.K.) | green later on blackish 147C | green 146D | green 138B |
| 4 | Seed yield (q/ha) | 11.61-12.83 | 8.80-9.81 | 10.61-11.12 |
| 5 | Straw yield )q/ha) | 8.91-9.25 | 7.23-7.87 | 8.21-8.89 |
| 6 | Constituents in opium | | | |
|  | Morphine % | 15.10-17.60 | 13.33-16.8 | 14.47-14.93 |
|  | Codeine % | 2.53-3.15 | 2.67-3.20 | 2.15-2.53 |
|  | Thebaine % | 1.78-2.80 | 1.47-2.53 | 1.47-1.87 |
|  | Narcotine % | 8.67-9.47 | 7.87-9.47 | 7.47-8.93 |
|  | Papaverine % | 0.00-0.13 | 0.00 | 0.00 |
| 7 | Days to 50% flowering | 108-110 | 106-108 | 108-112 |
| 8 | Days to maturity | 140-142 | 138-140 | 142-146 |
| 9 | Number of capsules/plant | 3-5 | 1-3 | 2-4 |
| 10 | No. of stigmatic rays/capsule | 12-14 | 13-14 | 14-16 |
| 11 | Latex colour | dark pink | Brown | dark brown |
| 12 | Number of seeds/g | 3515 | 2370 | 3430 |
| 13 | Seed colour | Whitish | Whitish | whitish |
| 14 | Leaf area (cm$^2$) | 179.2-181.8 | 175.1-177.1 | 184.6-189.2 |
| 15 | Pollen fertility (%) | 95-98 | 92-96 | 92-94 |
| 16 | Seed germination (%) | 94 | 92 | 93 |
| 17 | Oil content in seed (%) | 48 | 45 | 46 |
| 18 | Capsule shape | Spherical-real sphere | Spherical-real sphere | Flat spherical |
| 19 | Capsule surface | Smooth | Smooth | smooth |
| 20 | Leaf colour (Based on Royal Horticultural Society, London, U.K.) | Green, 147B | Green, 138A | Green, 137D |
| 21 | Stem diameter (cm) | 1.03-1.10 | 0.92-0.94 | 1.00-1.07 |
| 22 | Capsule size (cm$^2$) | 14.30-14.68 | 12.61-13.04 | 13.83-14.12 |
| 23 | Branches/plant | 3-6 | 1-3 | 2-4 |
| 24 | Opium yield (Kg/ha) | 64-68 | 45-48 | 52-54 |
| 25 | Capsule colour (Based on Royal Horticultural Society, London, U.K.) | Green, 147 B | Green, 138B | Green, 138B |

TABLE 2

Mean, heterosis (%) and inbreeding depression (%) in parents, their $F_1$s and $F_2$s in selected 7 promising crosses evaluated for preliminary trial in opium poppy.

| | | Opium yield | | | | | Seed yield | | | | | Morphine % | | | | |
|---|---|---|---|---|---|---|---|---|---|---|---|---|---|---|---|---|
| | | | Heterosis % | | | | | Heterosis % | | | | | Heterosis % | | | |
| | | Mean | M.P. | B.P. | E.P. | I.D. | Mean | M.P. | B.P. | E.P. | I.D. | Mean | M.P. | B.P. | E.P. | I.D. |
| Parents | | | | | | | | | | | | | | | | |
| BR003 | | 172.00 | | | | | 7.67 | | | | | 11.73 | | | | |
| BR009 | | 167.40 | | | | | 5.00 | | | | | 10.00 | | | | |
| BR010 | | 192.67 | | | | | 4.83 | | | | | 11.70 | | | | |
| BR006 | | 152.50 | | | | | 5.97 | | | | | 11.97 | | | | |
| BR007 | | 235.97 | | | | | 6.83 | | | | | 12.53 | | | | |
| BR005 | | 147.00 | | | | | 5.80 | | | | | 14.80 | | | | |
| BR008 | | 163.67 | | | | | 6.00 | | | | | 10.93 | | | | |
| BR001 | | 157.30 | | | | | 7.80 | | | | | 10.47 | | | | |
| NBRI-3 (EP) | | 229.70 | | | | | 7.50 | | | | | 13.50 | | | | |
| Crosses | | | | | | | | | | | | | | | | |
| BR003 × | $F_1$ | 264.53 | 55.80 | 53.70 | 15.16 | — | 8.33 | 31.49 | 8.60 | 11.60 | — | 13.87 | 27.65 | 18.24 | 2.74 | — |
| BR009 | $F_2$ | 190.77 | — | — | −16.94 | 27.88 | 6.37 | — | — | −15.06 | 23.52 | 14.33 | — | — | 6.14 | −3.31 |
| BR003 × | $F_1$ | 214.37 | 17.56 | 24.63 | −6.67 | — | 7.17 | 14.72 | −6.51 | −4.40 | — | 13.80 | 17.84 | 17.64 | 2.22 | — |
| BR010 | $F_2$ | 144.87 | — | — | −36.93 | 32.42 | 5.78 | — | — | −22.93 | 19.38 | 14.20 | — | — | 5.18 | −2.89 |
| BR006 × | $F_1$ | 202.50 | 24.80 | 32.78 | −11.84 | — | 5.17 | −24.19 | −13.40 | −31.06 | — | 12.87 | 8.60 | 7.51 | −4.66 | — |
| BR003 | $F_2$ | 214.27 | — | — | −6.71 | −5.81 | 5.37 | — | — | −28.40 | −3.86 | 12.13 | — | — | −10.14 | 5.74 |
| BR007 × | $F_1$ | 300.63 | 54.77 | 97.13 | 30.87 | — | 10.17 | 58.90 | 70.35 | 35.60 | — | 15.00 | 22.44 | 25.31 | 11.11 | — |
| BR006 | $F_2$ | 296.37 | — | — | 29.02 | 1.41 | 10.84 | — | — | 44.53 | −6.58 | 16.60 | — | — | 22.96 | −10.60 |
| BR010 × | $F_1$ | 234.93 | 22.68 | −0.44 | 2.27 | — | 6.87 | 8.78 | 0.58 | −8.40 | — | 13.73 | 0.47 | 9.57 | 1.70 | — |

TABLE 2-continued

Mean, heterosis (%) and inbreeding depression (%) in parents, their F₁s and F₂s in selected 7 promising crosses evaluated for preliminary trial in opium poppy.

| | | Opium yield | | | | | Seed yield | | | | | Morphine % | | | | |
|---|---|---|---|---|---|---|---|---|---|---|---|---|---|---|---|---|
| | | | Heterosis % | | | | | Heterosis % | | | | | Heterosis % | | | |
| | | Mean | M.P. | B.P. | E.P. | I.D. | Mean | M.P. | B.P. | E.P. | I.D. | Mean | M.P. | B.P. | E.P. | I.D. |
| BR005 | F₂ | 235.93 | — | — | 2.27 | −0.42 | 7.83 | — | — | 4.40 | −13.97 | 13.20 | — | — | −2.22 | 3.86 |
| BR008 × | F₁ | 220.03 | 37.10 | 34.43 | −4.20 | — | 7.67 | −11.15 | 28.47 | 2.26 | — | 11.40 | 6.54 | 4.30 | −15.55 | — |
| BR001 | F₂ | 243.13 | — | — | 5.84 | −10.49 | 7.03 | — | — | −6.26 | 8.34 | 12.13 | — | — | −10.19 | −6.40 |
| BR007 × | F₁ | 272.73 | 36.48 | 66.63 | 18.73 | — | 8.37 | 30.47 | 39.50 | 11.60 | — | 14.27 | 21.65 | 30.50 | 5.70 | — |
| BR008 | F₂ | 285.57 | — | — | 24.32 | −4.70 | 7.70 | — | — | 2.66 | 8.00 | 14.50 | — | — | 7.40 | −1.61 |

The invention is further elaborated with the help of following examples. These examples should not be construed to limit the scope of the invention.

EXAMPLE 1

Preliminary evaluation trial was conducted for 3 consecutive years (1990-91 to 1992-93) comprising 7 selected cross progenies (BR003×BR009, BR003×BR010, BR006×BR003, BR007×BR006, BR007×BR005, BR008×BR001 and BR007×BR008), which were started showing uniformity in the plant population of the particular cross against the released variety (BROP-1) as check. The trials were conducted in RBD with three replications in plot size 3 m² for each treatment/replication. The rows were 3 meter long with row-to-row spacing was 25 cm and plant to plant 10 cm. The results are presented in Tables 3-5, which exhibited that BR007×BR006 (Madakini) and BR007×BR008 performed best over all the 7 selected cross progenies and check. The "Madakini" (BR007×BR006) showed 43.45% increase over check for opium yield and 20.42% for seed yield and 10% for morphine content. These two elite lines were selected for evaluation in initial evaluation trial with 8 other new entries during the successive years (1993-94 to 1995-96).

TABLE 3

Preliminary Trial for Opium Yield (Kg/ha) in opium poppy.

| Crosses | 1990-91 | 1991-92 | 1992-93 | Mean ± SE | % increase over check |
|---|---|---|---|---|---|
| BR003 × BR009 | 48.14 | 63.04 | 57.47 | 56.22 ± 1.34 | 15.72 |
| BR003 × BR010 | 58.15 | 53.87 | 61.53 | 57.85 ± 2.21 | 19.08 |
| BR006 × BR003 | 42.60 | 40.53 | 38.47 | 40.53 ± 1.19 | −16.57 |
| BR007 × BR006 | 68.77 | 68.70 | 71.61 | 69.69 ± 0.95 | 43.45 |
| BR007 × BR005 | 47.41 | 48.08 | 38.62 | 44.70 ± 3.04 | −7.98 |
| BR008 × BR001 | 43.98 | 38.09 | 47.23 | 43.10 ± 2.67 | −11.28 |
| BR007 × BR008 | 69.80 | 60.97 | 64.60 | 65.12 ± 2.56 | 34.04 |
| BROP-1 (Check) | 46.54 | 54.93 | 44.26 | 48.57 ± 3.24 | |
| Mean | 53.17 | 53.52 | 52.97 | | |
| SE | 3.88 | 3.81 | 4.79 | | |

TABLE 4

Preliminary trial for Seed yield (q/ha) in opium poppy.

| Crosses | 1990-91 | 1991-92 | 1992-93 | Mean ± SE | % increase over check |
|---|---|---|---|---|---|
| BR003 × BR009 | 11.16 | 9.92 | 10.54 | 10.54 ± 7.07 | 5.50 |
| BR003 × BR010 | 8.56 | 12.64 | 9.54 | 10.58 ± 1.03 | 5.90 |
| BR006 × BR003 | 10.91 | 10.66 | 10.41 | 10.66 ± 0.14 | 6.70 |
| BR007 × BR006 | 12.26 | 11.91 | 11.93 | 12.03 ± 0.12 | 20.42 |
| BR007 × BR005 | 8.68 | 8.06 | 8.93 | 8.56 ± 0.26 | −14.31 |
| BR008 × BR001 | 9.92 | 9.92 | 10.04 | 9.96 ± 0.04 | −0.30 |
| BR007 × BR008 | 12.27 | 11.16 | 10.54 | 11.32 ± 0.50 | 13.31 |
| BROP-1 (Check) | 9.92 | 10.66 | 9.41 | 9.99 ± 0.36 | |
| Mean | 10.58 | 10.61 | 10.16 | | |
| SE | 3.99 | 4.01 | 3.82 | | |

TABLE 5

Preliminary trial for morphine content (%) in opium poppy.

| Crosses | 1990-91 | 1991-92 | 1992-93 | Mean ± SE | % increase over check |
|---|---|---|---|---|---|
| BR003 × BR009 | 12.40 | 13.00 | 13.20 | 12.87 ± 8.58 | −1.00 |
| BR003 × BR010 | 15.60 | 14.70 | 14.20 | 12.83 ± 9.80 | −1.30 |
| BR006 × BR003 | 13.60 | 12.00 | 13.00 | 12.87 ± 8.58 | −1.00 |
| BR007 × BR006 | 13.20 | 15.70 | 14.00 | 14.30 ± 9.56 | 10.00 |
| BR007 × BR005 | 11.00 | 11.60 | 11.20 | 11.27 ± 7.51 | −13.30 |
| BR008 × BR001 | 13.00 | 11.40 | 11.80 | 12.07 ± 8.05 | −7.15 |
| BR007 × BR008 | 13.20 | 13.20 | 14.60 | 13.13 ± 9.17 | 1.00 |
| BROP-1 (Check) | 14.00 | 12.60 | 12.40 | 13.00 ± 8.68 | |
| Mean | 13.25 | 13.02 | 13.07 | | |
| SE | 4.99 | 4.91 | 4.92 | | |

EXAMPLE 2

Initial evaluation trial laid out during 1993-94 to 1995-96 in RBD with 3 replications comprising two selected elite lines and 8 other new entries (BR007×BR006, BR007×BR008, BR300×S-18, S-10×S-18, S-10×S-7, NBRI-7, NBRI-8, S-18×S-16, BR334 and Shyama) along with a check (BROP-1). The plot size was 6 m² for each entry/replication with 8 rows. Rows were 3 meter in length and the spacing between row to row was 25 cm and plant to plant 10 cm. The results have been presented in Tables 6-9. Further, BR007×BR006 (Madakini) showed 33.87% increase over the best check for opium yield. Similarly, "Madakini" also showed 31.78% increase for seed yield and 18.56% for husk yield. The morphine content was also maximum in "Madakini" as compared to the best check BROP-1.

TABLE 6

Initial Evaluation Trial for Opium Yield (Kg/ha) in opium poppy.

| Crosses | 1993-94 | 1994-95 | 1995-96 | Mean ± SE | % increase over check |
|---|---|---|---|---|---|
| BR007 × BR006 | 77.64 | 69.21 | 64.65 | 70.50 ± 3.80 | 33.87 |
| BR007 × BR008 | 65.86 | 56.72 | 60.27 | 60.95 ± 2.66 | 15.74 |
| BR300 × S-18 | 48.63 | 47.20 | 47.25 | 47.69 ± 0.46 | −9.43 |
| S-10 × S-18 | 52.62 | 46.00 | 49.94 | 49.52 ± 1.92 | −5.96 |
| S-10 × S-7 | 50.74 | 48.72 | 48.70 | 49.39 ± 0.67 | −6.20 |
| NBRI-7 | 51.88 | 58.18 | 59.74 | 56.60 ± 2.40 | 7.48 |
| NBRI-8 | 52.76 | 48.83 | 52.76 | 51.45 ± 1.31 | −2.29 |
| S-18 × S-16 | 49.51 | 41.39 | 53.59 | 48.16 ± 3.58 | −8.54 |
| BR334 | 52.78 | 43.63 | 50.99 | 49.13 ± 3.79 | −6.70 |
| Shyama | 48.28 | 45.51 | 51.50 | 48.43 ± 1.73 | −8.03 |
| BROP-1 | 51.12 | 55.17 | 51.70 | 52.66 ± 1.35 | |
| Mean | 54.71 | 50.92 | 53.73 | | |
| SE | 2.70 | 2.45 | 1.64 | | |

TABLE 7

Initial Evaluation Trial for seed Yield (q/ha) in opium poppy.

| Crosses | 1993-94 | 1994-95 | 1995-96 | Mean ± SE | % increase over check |
|---|---|---|---|---|---|
| BR007 × BR006 | 11.76 | 10.56 | 12.52 | 11.61 ± 0.57 | 31.78 |
| BR007 × BR008 | 9.87 | 9.42 | 10.83 | 10.04 ± 0.41 | 13.96 |
| BR300 × S-18 | 9.38 | 10.83 | 10.28 | 10.16 ± 0.42 | 15.32 |
| S-10 × S-18 | 8.21 | 6.90 | 7.38 | 7.49 ± 0.38 | −14.98 |
| S-10 × S-7 | 7.18 | 8.97 | 9.25 | 8.46 ± 0.64 | −3.97 |
| NBRI-7 | 8.97 | 7.15 | 9.06 | 8.39 ± 0.62 | −4.76 |
| NBRI-8 | 9.31 | 8.02 | 9.39 | 8.90 ± 0.44 | 1.02 |
| S-18 × S-16 | 7.70 | 8.90 | 8.87 | 8.49 ± 0.39 | −3.63 |
| BR334 | 7.10 | 9.62 | 8.90 | 8.54 ± 0.75 | −3.06 |
| Shyama | 6.50 | 7.00 | 6.30 | 6.60 ± 0.20 | −25.08 |
| BROP-1 | 9.13 | 8.97 | 8.35 | 8.81 ± 0.23 | |
| Mean | 8.64 | 8.75 | 9.19 | | |
| SE | 0.45 | 0.41 | 0.50 | | |

TABLE 8

Initial Evaluation Trial for husk yield (q/ha) in opium poppy.

| Crosses | 1993-94 | 1994-95 | 1995-96 | Mean ± SE | % increase over check |
|---|---|---|---|---|---|
| BR007 × BR006 | 11.11 | 10.80 | 12.21 | 11.37 ± 0.42 | 18.56 |
| BR007 × BR008 | 10.73 | 12.07 | 10.14 | 11.31 ± 1.59 | 17.93 |
| BR300 × S-18 | 8.97 | 10.35 | 11.52 | 10.28 ± 1.45 | 7.19 |
| S-10 × S-18 | 10.28 | 10.14 | 11.32 | 10.58 ± 1.49 | 10.32 |
| S-10 × S-7 | 10.21 | 11.38 | 11.80 | 11.13 ± 1.57 | 16.05 |
| NBRI-7 | 9.12 | 8.10 | 8.75 | 8.65 ± 1.22 | −9.80 |
| NBRI-8 | 9.00 | 7.80 | 8.15 | 8.31 ± 1.17 | −13.34 |
| S-18 × S-16 | 6.70 | 8.10 | 8.50 | 7.76 ± 1.10 | −19.08 |
| BR334 | 6.50 | 8.50 | 8.15 | 7.71 ± 1.09 | −19.60 |
| Shyama | 6.15 | 6.50 | 5.80 | 6.15 ± 0.86 | −35.87 |
| BROP-1 | 9.25 | 9.28 | 10.25 | 9.59 ± 1.35 | |
| Mean | 9.00 | 9.36 | 9.69 | | |
| SE | 0.56 | 0.51 | 0.94 | | |

TABLE 9

Initial Evaluation Trial for Morphine content (%) in opium poppy.

| Crosses | 1993-94 | 1994-95 | 1995-96 | Mean + SE | % increase over check |
|---|---|---|---|---|---|
| BR007 × BR006 | 16.6 | 17.8 | 16.6 | 17.00 ± 0.40 | 12.80 |
| BR007 × BR008 | 17.4 | 16.6 | 16.2 | 16.73 ± 0.36 | 11.01 |
| BR300 × S-18 | 15.2 | 16.0 | 15.6 | 15.60 ± 0.33 | 3.51 |
| S-10 × S-18 | 13.8 | 14.8 | 14.8 | 14.47 ± 0.33 | −3.98 |
| S-10 × S-7 | 14.8 | 13.6 | 14.0 | 14.13 ± 0.35 | −6.23 |
| NBRI-7 | 14.0 | 13.0 | 14.8 | 13.93 ± 0.52 | −7.56 |
| NBRI-8 | 13.8 | 14.4 | 13.2 | 13.80 ± 0.34 | −8.42 |
| S-18 × S-16 | 13.2 | 15.6 | 13.2 | 14.00 ± 0.80 | −7.10 |
| BR334 | 15.2 | 13.0 | 14.0 | 14.07 ± 0.63 | −6.63 |
| Shyama | 11.3 | 12.0 | 11.8 | 11.70 ± 0.20 | −22.36 |
| BROP-1 | 14.8 | 15.2 | 15.2 | 15.07 ± 0.14 | |
| Mean | 14.55 | 14.73 | 14.49 | | |
| SE | 0.50 | 0.53 | 0.44 | | |

EXAMPLE 3

Multilocational trials were laid out for 3 consecutive years during 1996-97 to 1998-99 in RBD with 3 replications including other locations entries (BR007×BR006, BR007×BR008, NBPGR-1, NBPGR-2, MOP-204, ND-11-86, MOP-1072, MOP-1077) alongwith a local check (BROP-1) and a national check (IC-42) Tables 10-13. BR007×BR006 (Madakini) recorded maximum opium yield over other entries in all the 3 years. "Madakini" recorded 67.01 kg/ha opium yield as compared to 52.76 kg/ha of BROP-1 and 45.25 kg/ha of IC-42, which is 15.6% and 48.08% increase over check respectively. Similarly, seed yield of "Madakini" was noticed up to 11.77 q/ha over 3 years trials in comparison to 10.19 q/ha of BROP-1 and 7.66 q/ha of IC-42. Increase in seed yield of "Madakini" was 15.5% and 53.65% over BROP-1 and IC-42 respectively. The increase of 16.91% over BROP-1 and 40.71% over IC-42 was found for husk yield in "Madakini". The morphine content was also comparably higher in "Madakini". The increase in morphine content over local and national check was 18.45% and 28.60% respectively.

TABLE 10

Multilocational Trial for Opium yield (kg/ha) in opium poppy.

| Crosses | 1996-97 | 1997-98 | 1998-99 | Mean ± SE | % increase over check Local | % increase over check National |
|---|---|---|---|---|---|---|
| NBPGR-1 | 51.10 | 54.20 | 49.30 | 51.53 ± 1.43 | −2.33 | 13.87 |
| NBPGR-2 | 53.89 | 52.37 | 52.25 | 52.84 ± 0.88 | 0.15 | 16.77 |
| BR007 × BR006 | 68.84 | 62.65 | 69.53 | 67.01 ± 2.18 | 15.6 | 48.08 |
| BR007 × BR008 | 67.38 | 58.73 | 61.48 | 62.53 ± 2.55 | 18.51 | 38.18 |
| MOP-204 | 53.11 | 53.53 | 50.57 | 52.40 ± 0.39 | −0.68 | 15.80 |
| ND-11-86 | 52.53 | 43.62 | 47.99 | 48.00 ± 2.57 | −9.02 | 6.07 |
| MOP-1072 | 41.26 | 40.83 | 41.13 | 41.07 ± 0.12 | −22.15 | −9.23 |
| MOP-1077 | 38.42 | 36.73 | 36.53 | 37.23 ± 0.60 | −29.43 | −17.72 |
| BROP-1 (Local check) | 52.0 | 50.57 | 55.02 | 52.76 ± 1.28 | | 16.59 |
| IC-42 (National check) | 44.71 | 46.29 | 44.74 | 45.25 ± 0.52 | −14.23 | |
| Mean | 52.39 | 49.75 | 50.85 | 51.07 | | |
| SE | 3.12 | 2.55 | 3.03 | 2.84 | | |

TABLE 11

Multilocational Trial for Seed yield (q/ha) in opium poppy.

| Crosses | 1996-97 | 1997-98 | 1998-99 | Mean ± SE | % increase over check Local | % increase over check National |
|---|---|---|---|---|---|---|
| NBPGR-1 | 7.90 | 8.06 | 7.01 | 7.66 ± 0.32 | −24.82 | 0.00 |
| NBPGR-2 | 9.04 | 8.87 | 9.04 | 8.98 ± 0.33 | −11.87 | 17.23 |
| BR007 × BR006 | 12.84 | 11.37 | 11.11 | 11.77 ± 0.53 | 15.50 | 53.65 |
| BR007 × BR008 | 10.98 | 10.82 | 9.16 | 10.32 ± 0.58 | 1.27 | 34.72 |
| MOP-204 | 6.36 | 7.87 | 9.37 | 7.87 ± 0.86 | −22.76 | 2.74 |
| ND-11-86 | 7.20 | 6.51 | 7.45 | 7.05 ± 0.28 | −30.81 | −7.96 |
| MOP-1072 | 8.68 | 7.52 | 7.87 | 8.02 ± 0.34 | −21.29 | 4.69 |
| MOP-1077 | 7.00 | 8.00 | 7.65 | 7.55 ± 0.29 | −25.90 | −1.43 |
| BROP-1 (Local check) | 9.34 | 10.86 | 10.37 | 10.19 ± 0.44 | | 33.02 |
| IC-42 (National check) | 8.05 | 7.58 | 7.36 | 7.66 ± 0.20 | −24.82 | |
| Mean | 8.74 | 8.75 | 8.64 | 8.71 ± 0.49 | | |
| SE | 0.62 | 0.53 | 0.44 | | | |

TABLE 12

Multilocational Trial for husk yield (q/ha) in opium poppy.

| Crosses | 1996-97 | 1997-98 | 1998-99 | Mean ± SE | % increase over check Local | % increase over check National |
|---|---|---|---|---|---|---|
| NBPGR-1 | 7.56 | 9.12 | 7.40 | 8.03 ± 0.55 | −8.85 | 9.69 |
| NBPGR-2 | 9.88 | 8.74 | 9.04 | 9.22 ± 0.35 | 4.65 | 25.95 |
| BR007 × BR006 | 10.77 | 10.64 | 9.50 | 10.30 ± 0.40 | 16.91 | 40.71 |
| BR007 × BR008 | 9.56 | 10.07 | 9.02 | 9.55 ± 0.30 | 8.39 | 30.46 |
| MOP-204 | 6.71 | 7.69 | 7.75 | 7.38 ± 0.33 | −16.23 | 0.81 |
| ND-11-86 | 6.83 | 6.46 | 7.60 | 6.96 ± 0.33 | −20.99 | −4.91 |
| MOP-1072 | 7.71 | 7.03 | 6.53 | 7.09 ± 0.35 | −19.52 | −3.14 |
| MOP-1077 | 6.77 | 7.84 | 7.64 | 7.42 ± 0.33 | −15.77 | 1.36 |
| BROP-1 (Local check) | 8.56 | 9.12 | 8.74 | 8.81 ± 0.17 | | 20.35 |
| IC-42 (National check) | 6.63 | 7.63 | 7.69 | 57.32 ± 0.35 | −16.91 | |
| Mean | 8.09 | 8.43 | 8.09 | 8.21 | | |
| SE | 0.48 | 0.42 | 0.29 | 0.37 | | |

TABLE 13

Multilocational Trial for Morphine content (%) in opium poppy.

| Crosses | 1996-97 | 1997-98 | 1998-99 | Mean ± SE | % increase over check Local | National |
|---|---|---|---|---|---|---|
| NBPGR-1 | 14.8 | 13.2 | 15.2 | 14.40 ± 0.61 | 9.33 | 18.71 |
| NBPGR-2 | 15.2 | 14.8 | 14.8 | 14.93 ± 0.14 | 13.36 | 23.08 |
| BR007 × BR006 | 16.4 | 15.2 | 15.2 | 15.60 ± 0.40 | 18.45 | 28.60 |
| BR007 × BR008 | 16.6 | 15.2 | 14.8 | 15.53 ± 0.55 | 17.91 | 28.02 |
| MOP-204 | 13.2 | 14.0 | 13.6 | 13.60 ± 0.22 | 3.26 | 12.11 |
| ND-11-86 | 13.6 | 11.4 | 13.6 | 12.87 ± 73 | −2.27 | 6.10 |
| MOP-1072 | 13.8 | 12.3 | 14.8 | 13.63 ± 0.73 | 3.49 | 12.36 |
| MOP-1077 | 13.7 | 12.2 | 13.2 | 13.03 ± 0.45 | −1.06 | 7.41 |
| BROP-1 (Local check) | 12.3 | 13.4 | 13.8 | 13.17 ± 0.45 | | 8.57 |
| IC-42 (National check) | 11.6 | 12.2 | 12.6 | 12.13 ± 0.30 | −7.89 | |
| Mean | 14.12 | 13.39 | 14.16 | | | |
| SE | 0.52 | 0.44 | 0.28 | | | |

EXAMPLE 4

The newly developed variety "Madakini" and their parents (BR006 and BR007) were screened for several fungal diseases viz. downy mildew, damping off, collar rot, powdery mildew, leaf spot and blight and stem/capsule rot for two consecutive years during 1999-2000 to 2000-01 in RBD with 3 replications in field with known history of sick soil for the past 20 years under natural epiphytotic conditions. The varieties IC-42 and BROP-1 served as National and Local State checks in screening for disease resistance. The newly developed variety "Madakini" was found to be resistant to downy mildew and powdery mildew and tolerant to damping off, collar rot, leaf spot and blight and stem/capsule rot disease (Table 14).

TABLE 14

Comparative performance of parents and variety "Madakini" against various fungal diseases under field conditions.

| | Germplasm/variety | | | | | | | | | |
|---|---|---|---|---|---|---|---|---|---|---|
| | IC-42 | | BROP-1 | | BR006 | | BR007 | | Mandakini | |
| Diseases | 1999-2000 | 2000-2001 | 1999-2000 | 2000-2001 | 1999-2000 | 2000-2001 | 1999-2000 | 2000-2001 | 1999-2000 | 2000-2001 |
| Downey mildew | 2.39 | 2.83 | 6.39 | 5.11 | 1.91 | 1.39 | 4.73 | 4.79 | 0.99 | 0.91 |
| Damping off | 3.67 | 2.91 | 2.27 | 2.09 | 1.33 | 2.67 | 2.37 | 2.51 | 0.87 | 1.11 |
| Collar rot | 2.09 | 1.77 | 2.79 | 1.91 | 2.45 | 2.51 | 1.67 | 1.29 | 1.23 | 1.05 |
| Powdery mildew | 2.17 | 1.93 | 2.37 | 1.89 | 1.83 | 2.17 | 2.47 | 2.33 | 0.93 | 1.07 |
| Leaf spot and blight | 2.67 | 3.33 | 4.67 | 5.33 | 2.33 | 2.57 | 2.89 | 3.67 | 1.33 | 1.91 |
| Stem/capsule rot | 1.39 | 2.33 | 1.39 | 1.57 | 2.45 | 2.79 | 2.39 | 3.91 | 1.29 | 1.67 |

Stability Performance

The variety "Madakini" showed stable performance for all its quantitative, qualitative and physiological characteristics for the last 6 years at NBRI experimental field with different competitive lines of local as well as of different locations. The disease rating was also observed consistent and uniform against all the major diseases scored during the last two years of experimentation.

Statement of Distinction

As evident from the morpho physiology, new variety "Madakini" is distinct from its parents as well as other existing varieties by having new combination of plant traits. The vigorous plant habit with blackish peduncle at the bottom of capsule during maturity of the capsules, dark green leaves, significantly high opium yield (up to 68 kg/ha) and seed yield (up to 12 q/ha) as compared to BROP-1. The variety also recorded high morphine content and other alkaloids in comparison to the existing varieties/lines.

The invention claimed is:

1. An opium poppy (*Papaver somniferum* L.) plant designated cultivar 'Madakini' obtained from seed deposited at the National Collections of Industrial, Food and Marine Bacteria (NCIMB Ltd.), Scotland, United Kingdom, with the accession number NCIMB 41506, and having the following characteristics:
   a. opium yield of about 64-68 kg/ha;
   b. oil content in seed of about 48-49%; wherein fatty acid composition of the oil is palmitic acid 9.0%, steraic acid 2.1%, oleic acid 18.4%, linoleic acid 70.1% linolenic acid 0.4%, unsaturated total fatty acid 88.9% and saturated fatty acid 11.1%; and
   c. opium latex contains morphine 15.0-17.60%, codeine 2.53-3.15%, thebaine 1.78-2.80%, narcotine 8.67-9.47% and papaverine 0.00-0.13%.

2. A seed of opium poppy (*Papaver somniferum* L.) deposited at the NCIBM Ltd., Scotland, United Kingdom, having accession number NCIMB 41506.

* * * * *